(12) United States Patent
Ma et al.

(10) Patent No.: US 9,511,366 B2
(45) Date of Patent: Dec. 6, 2016

(54) MICROFLUIDIC DEVICE AND ITS USE FOR POSITIONING OF CELLS OR ORGANISMS

(75) Inventors: Rui Ma, Beijing (CN); Lan Xie, Beijing (CN); Tian Qiu, Beijing (CN); Lei Wang, Beijing (CN); Wanli Xing, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 13/991,848

(22) PCT Filed: Jan. 13, 2012

(86) PCT No.: PCT/CN2012/000065
§ 371 (c)(1),
(2), (4) Date: Sep. 9, 2013

(87) PCT Pub. No.: WO2012/094956
PCT Pub. Date: Jul. 19, 2012

(65) Prior Publication Data
US 2014/0004557 A1 Jan. 2, 2014

(30) Foreign Application Priority Data
Jan. 13, 2011 (CN) .......................... 2011 1 0006837

(51) Int. Cl.
*B01L 3/00* (2006.01)
*C12M 3/00* (2006.01)
(Continued)

(52) U.S. Cl.
CPC ............. *B01L 3/5027* (2013.01); *C12M 21/06* (2013.01); *C12M 23/12* (2013.01); *C12M 23/16* (2013.01)

(58) Field of Classification Search
CPC ... B01L 3/5027; C12M 23/12; C12M 23/16; C12M 21/06
See application file for complete search history.

(56) References Cited

U.S. PATENT DOCUMENTS

| 5,427,946 A | 6/1995 | Kricka et al. |
| 6,193,647 B1 | 2/2001 | Beebe et al. |

(Continued)

FOREIGN PATENT DOCUMENTS

| CN | 1909847 | 2/2007 |
| CN | 101597568 | 12/2009 |

(Continued)

OTHER PUBLICATIONS

Farooq and Norton, "A modified procedure for isolation of astrocyte- and neuron-enriched fractions from rat brain," J Neurochem (1978) 31(4):887-894.

(Continued)

*Primary Examiner* — Lore Jarrett
(74) *Attorney, Agent, or Firm* — Morrison & Foerster LLP (57) ABSTRACT

A micro fluidic device comprises one microstructure layer (5) and one cover layer (1), wherein the cover layer (1) is connected to the microstructure layer (5). The microstructure layer (5) comprises one bottom layer and a plurality of microstructures on it to position samples. The cover layer (1) comprises one top layer, one positioning well (6) and at least one inlet pool (4). The positioning well (6) is right above the microstructures and connected with each other. The inlet pools (4) and the positioning well (6) are connected by microchannels (3) which are formed between the microstructure layer (5) and the cover layer (1). The micro fluidic device can be applied in vitro fertilization, in determining how glial cells affect neurons, in constructing neural network and in detecting cell growth conditions.

30 Claims, 8 Drawing Sheets (51) Int. Cl.
C12M 1/32 (2006.01)
C12M 3/06 (2006.01)

(56) References Cited

U.S. PATENT DOCUMENTS

| | | | |
|---|---|---|---|
| 6,448,069 | B1 | 9/2002 | Cecchi et al. |
| 2003/0017467 | A1* | 1/2003 | Hooper et al. ............. 435/6 |
| 2004/0142411 | A1 | 7/2004 | Kirk et al. |
| 2006/0270021 | A1 | 11/2006 | Takayama et al. |
| 2007/0264705 | A1 | 11/2007 | Dodgson |
| 2010/0111770 | A1 | 5/2010 | Hwang et al. |
| 2011/0183312 | A1 | 7/2011 | Huang |

FOREIGN PATENT DOCUMENTS

| | | |
|---|---|---|
| CN | 101827931 | 9/2010 |
| CN | 101914435 | 12/2010 |
| WO | WO-2004/108011 | 12/2004 |
| WO | WO-2009/006933 | 1/2009 |
| WO | WO-2009/062095 | 5/2009 |
| WO | WO-2012/019436 | 2/2012 |

OTHER PUBLICATIONS

International Preliminary Report on Patentability and Written Opinion for PCT/CN2012/000065, issued Jul. 16, 2013, 5 pages.
International Search Report for PCT/CN2012/000065, mailed Mar. 29, 2012, 5 pages.
McCarthy and Vellis, "Preparation of separate astroglial and oligodendroglial cell cultures from rat cerebral tissue," J Cell Biol (1980) 85(3):890-902.
Whitesides, "The origins and the future of microfluidics," Nature (2006) 442:368-373.
International Search Report for PCT/CN2011/001329, mailed Nov. 17, 2011, 3 pages.
Koyama et al., "Chemotaxis assays of mouse sperm on microfluidic devices," Anal. CheM. (2006) 78:3354-9.
Whitesides, "The origins and the future of microfluidics," Nature (2006) 442:368-73.
Written Opinion for PCT/CN2011/001329, mailed Nov. 17, 2011, 7 pages.
Xie et al., "Integration of sperm motility and chemotaxis screening with a microchannel-based device," Clinical Chemistry (2010) 56(8):1270-1278.
Restriction Requirement for U.S. Appl. No. 13/814,426, issued Oct. 28, 2014, 11 pages.
Response to Restriction Requirement for U.S. Appl. No. 13/814,426, filed Dec. 18, 2014, 8 pages.
Office Action for U.S. Appl. No. 13/814,426, issued Jan. 23, 2015, 8 pages.

* cited by examiner

MICROFLUIDIC DEVICE AND ITS USE FOR POSITIONING OF CELLS OR ORGANISMS

CROSS-REFERENCE TO RELATED APPLICATIONS

This application is the national phase of PCT application PCT/CN2012/000065 having an international filing date of Jan. 13, 2012, which claims priority to Chinese Patent Application No. 201110006837.3, filed on Jan. 13, 2011. The contents of the above-listed applications are incorporated herein by this reference in their entireties.

TECHNICAL FIELD

The present invention relates to a microfluidic device and its uses for positioning of cells or organisms. This microfluidic device comprises functional microstructures for positioning of one or more cells/organisms, and, in some embodiments symmetrically aligned microchannels for cell motility screening.

BACKGROUND ART

Microfluidic technology refers to a reaction system which could handle a small amount of liquid or samples ($10^{-9}$-$10^{-18}$ L) in microchannels in the scale of tens to hundreds of microns (Whitesides, *Nature* (2006) 442:368-73). The first application of microfluidic technology in biochemical analysis is the research of capillary electrophoresis. Because of its rapid and high-throughput analysis capability on small sample volumes and its high sensitivity and integration, microfluidic technology has been introduced to research and analysis at the levels of molecules (e.g., nucleic acid, protein, etc.), cells, tissues and organisms.

Cell positioning in a research system is usually the basis for the mechanism study of cell physiology. For example, cells are usually restricted in a fixed position for stable experimental conditions and continuous observations, in the studies of cell metabolism, cell growth and development and cell-environment interactions, etc. In the meanwhile, the distribution of cells in some special studies is also important. For example, the signal transmission between neurons can be very different due to the different arrangement of cells. In addition, motility screening of specific cells, cell culture and dynamic monitoring of cell conditions are also indispensable for mechanism studies of cells. Currently, microfluidic technology has been widely used in cell positioning, cell sorting, culture medium displacement and cell detection. However, a microdevice integrating all aforementioned steps is yet to be developed. The demand for such devices is even more urgent in the field of in vitro fertilization (IVF). IVF is a process by which egg cells are fertilized by sperm outside the body. The technology has become important treatment for human infertility. The major steps of conventional IVF include gamete collection, sperm motility screening, oocytes fertilization, medium replacement and early embryo culture. Since all the steps are conducted in Petri dish or tubes except oocyte collection, it's difficult to maintain a hemostasis with stable temperature and humidity. Besides, the conventional method is labor-intensive and poorly integrated. Therefore, a microdevice integrating cell positioning, cell motility screening, cell interaction, medium replacement and cell dynamic monitoring would be beneficial for improved IVF and assisted reproductive technology.

A microfluidic device was disclosed for embryo handling in U.S. Pat. No. 6,193,647. A constriction structure is included in their microdevice and an embryo can be parked at a desired location with the design. However, this device failed to select a single embryo out of a group, and it's not convenient for positioning and retrieval when dealing with more than one embryo. Moreover, shear force can hardly be avoided due to the constriction structure. John R. Dodgson et al. disclosed an apparatus for manipulation of cell, embryo or oocyte (Chinese Patent Application No. 200480033049.1). A well array is set in the microchannel and a fluidic passage is introduced to each well. This apparatus is suitable for handling of a group of more than two cells with multiple wells. However, the communication between the cells in adjacent wells is highly limited without gaps between the wells and it's difficult to build up of beneficial auto/paracrine factors from cell-cell contact or cell-environment crosstalk.

SUMMARY OF THE INVENTION

The present invention relates to a microfluidic device and its use for positioning cells or organisms. Therefore, in one aspect, provided herein is a microfluidic device for positioning a cell or organism, which device comprises: a) a microstructure layer comprising a plurality of microstructures on a bottom layer; and b) a cover layer comprising a positioning well and at least one inlet pool, wherein said inlet pool and said positioning well are in fluid connection by a microchannel, wherein said cover layer is connected to said microstructure layer, and said positioning well aligns with and/or is in fluid connection with said microstructures.

In some embodiments, the cross-section of the microstructure may be closed or partially closed. In some embodiments, the microstructure may comprise about 2, 4, 6, 8, 10 or more columns, wherein the cross-section of each column may be arc-shaped, square, triangular, circular, or another shape. In some embodiments, the microstructure layer may comprise about 2-10, 10-100, 100-1000 or more microstructures. In some embodiments, the cross-section of the microstructure may be polygon, preferably square, regular hexagon or octagon, or circle. In some embodiments, the microfluidic device may comprise about 2-8 inlet pools, preferably symmetrically distributed around the positioning well. In some embodiments, the gap between the columns may be smaller than the diameter of the cell or organism. In some embodiments, the depth of the microstructure may be larger than the diameter of the cell or organism. In some embodiments, the depth of the microstructure may be about 10-500 μm. In some embodiments, the microstructure layer and/or the cover layer may be about 1-10 mm, preferably about 2-10 mm, thick. In some embodiments, the diameter of the inlet pool may be about 1-10 mm, preferably about 2-10 mm. In some embodiments, the diameter of the positioning well may be about 1-100 mm, preferably about 2-100 mm. In some embodiments, the depth of the microchannel may be about 5-500 μm, preferably about 10-500 μm. In some embodiments, the microchannel may be about 2-100 mm in length and about 5 μm-2 mm in width. In some embodiments, the device may further comprise an oil-holding layer connected to the cover layer and above the positioning well and inlet pools. In some embodiments, the device may further comprise a basal layer connected to the microstructure layer. In some embodiments, the basal layer, the microstructure layer, the cover layer and/or the oil-holding layer may be made of glass or polydimethylsiloxane (PDMS).

In another aspect, provided herein is a system for positioning a cell or organism, which comprises the microfluidic device disclosed herein and a cell or organism in the microstructure. In some embodiments, the cell may be selected from the group consisting of an animal cell, a plant cell, a fungal cell, a bacterial cell, a recombinant cell and a cultured cell. In some embodiments, the cell may be an oocyte, a neuron, or another cell type. In some embodiments, the organism may be a bacterium, yeast, *C. elegans*, etc. In some embodiments, the system may further comprise a second type of cell or organism. In some embodiments, the system may further comprise an electrode in the microstructure.

In a further aspect, provided herein is a method for in vitro fertilization, which comprises: a) adding a plurality of oocytes into the positioning well of the microfluidic device disclosed herein filled with a first fluid; b) letting said oocytes position in the microstructures; c) adding a plurality of sperms into the inlet pools; d) adding mineral oil into the oil-holding layer; and e) incubating said microfluidic device under suitable conditions for in vitro fertilization. In some embodiments, the suitable conditions may include humidification, about 25-37° C., and about 1-10% $CO_2$. In some embodiments, the method may further comprise: f) replacing the first fluid with a second fluid followed by further incubation. In some embodiments, the method may further comprise embryo in situ staining and/or retrieval.

Also provided herein is a method for determining how glial cells affect neurons, which comprises: a) adding a plurality of neurons into the positioning well of the microfluidic device disclosed herein filled with a first fluid; b) letting said neurons plant in the microstructures; c) adding a plurality of glial cells into the inlet pools; d) adding mineral oil into the oil-holding layer; and e) incubating said microfluidic device under suitable conditions for neuronal growth. In some embodiments, the suitable conditions may include humidification, about 25-37° C., and about 1-10% $CO_2$. In some embodiments, the method may further comprise: f) replacing the first fluid with a second fluid followed by further incubation. In some embodiments, different types of glial cells may be added into separate inlet pools, wherein the glial cells may be selected from the group consisting of astrocytes, microglia, oligodendrocytes and fibroblasts.

Further provided herein is a method for constructing a neural network, which comprises: a) adding a plurality of neurons into the positioning well of the microfluidic device disclosed herein filled with a first fluid; b) letting said neurons plant in the microstructures; c) adding mineral oil into the oil-holding layer; d) incubating said microfluidic device under suitable conditions for neuronal growth; and e) replacing the first fluid with a second fluid followed by further incubation. In some embodiments, the suitable conditions may include humidification, about 25-37° C., and about 1-10% $CO_2$. In some embodiments, each microstructure may comprise two columns, and the cross-section of each column may be arc-shaped and a wider-inside-narrower-outside gap exists between the two columns.

In some embodiments, the method may further comprise: i) placing a detection electrode inside the microstructure; ii) connecting the electrode to an external signal source and signal detection device; and iii) performing cell growth detection through analyzing electrical signals from the electrode. In some embodiments, the electrical signals may be voltage, current or impedance, etc.

BRIEF DESCRIPTION OF THE DRAWINGS

FIGS. 12A-12C show schematic views of an exemplary microfluidic device.

A) Top view of the exemplary microfluidic device; B) Sectional view of the exemplary microfluidic device; C) Amplified view of one microstructure.

DETAILED DESCRIPTION OF THE INVENTION

This invention provides a microfluidic device and its uses for positioning cells or organisms.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

As used herein, the term "microfluidic device" generally refers to a device through which materials, particularly fluid borne materials, such as liquids, can be transported, in some embodiments on a micro-scale, and in some embodiments on a nanoscale. Thus, the microfluidic devices described by the presently disclosed subject matter can comprise microscale features, nanoscale features, and combinations thereof.

Accordingly, an exemplary microfluidic device typically comprises structural or functional features dimensioned on the order of a millimeter-scale or less, which are capable of manipulating a fluid at a flow rate on the order of a µL/min or less. Typically, such features include, but are not limited to channels, fluid reservoirs, reaction chambers, mixing chambers, and separation regions. In some examples, the channels include at least one cross-sectional dimension that is in a range of from about 0.1 µm to about 500 µm. The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current, and the like.

As used herein, the terms "channel," "micro-channel," "fluidic channel," and "microfluidic channel" are used interchangeably and can mean a recess or cavity formed in a material by imparting a pattern from a patterned substrate into a material or by any suitable material removing technique, or can mean a recess or cavity in combination with any suitable fluid-conducting structure mounted in the recess or cavity, such as a tube, capillary, or the like.

As used herein, the terms "flow channel" and "control channel" are used interchangeably and can mean a channel in a microfluidic device in which a material, such as a fluid, e.g., a gas or a liquid, can flow through. More particularly, the term "flow channel" refers to a channel in which a material of interest, e.g., a solvent or a chemical reagent, can flow through. Further, the term "control channel" refers to a flow channel in which a material, such as a fluid, e.g., a gas or a liquid, can flow through in such a way to actuate a control mechanism, such as a valve or pump.

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

As used herein, the term "microstructure" refers to a microscale feature that is used to position cells or organisms. A microstructure has a scale suitable for the positioning of individual cells or organisms, and may have any suitable shape, such as circle, square, etc. A microstructure may be attached to the surface of a chip at one end and has an opening at the other end for the cell or organism to enter. The wall of a microstructure prevents the cell or organism to exit, but may contain openings that allow molecules such as cytokines to enter/exit. The number and distribution of microstructures on a chip are determined by the purposes of the microfluidic device, such as IVF, cell growth detection, neural network formation, etc.

As used herein, the term "oocyte" refers to a female gamete cell and includes primary oocytes, secondary oocytes and mature, unfertilized ovum. An oocyte is a large cell having a large nucleus (i.e., the germinal vesicle) surrounded by ooplasm. The ooplasm contains non-nuclear cytoplasmic contents including mRNA, ribosomes, mitochondria, yolk proteins, etc. The membrane of the oocyte is referred to herein as the "plasma membrane."

As used herein, "medium" or "culture medium" refers to a fluidic carrier, e.g., liquid or gas, wherein cells are dissolved, suspended or contained.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

B. Microfluidic Device and Microfluidic System

In one aspect, provided herein is a microfluidic device for positioning a cell or organism, which device comprises: a) a microstructure layer comprising a plurality of microstructures on a bottom layer; and b) a cover layer comprising a positioning well and at least one inlet pool, wherein said inlet pool and said positioning well are in fluid connection by a microchannel, wherein said cover layer is connected to said microstructure layer, and said positioning well aligns with and/or is in fluid connection with said microstructures.

A microstructure may have a scale suitable for the positioning of individual cells or organisms, and may have any suitable shape, such as circle, square, etc. In some embodiments, the cross-section of the microstructure may be polygon, preferably square, regular hexagon or octagon, or circle. In some embodiments, the cross-section of the microstructure may be closed or partially closed. In some embodiments, the microstructure may comprise about 2, 4, 6, 8, 10 or more columns, wherein the cross-section of each column may be arc-shaped, square, triangular, circular, or another shape. In some embodiments, the gap between the columns may be smaller than the diameter of the cell or organism. In some embodiments, the depth of the microstructure may be larger than the diameter of the cell or organism. In some embodiments, the depth of the microstructure may be about 10-500 m. In some embodiments, the microstructure layer and/or the cover layer may be about 1-10 mm, preferably about 2-10 mm, thick. In some embodiments, the diameter of the inlet pool may be about 1-10 mm, preferably about 2-10 mm. In some embodiments, the diameter of the positioning well may be about 1-100 mm, preferably about 2-100 mm. In some embodiments, the depth of the microchannel may be about 5-500 µm, preferably about 10-500 µm. In some embodiments, the microchannel may be about 2-100 mm in length and about 5 µm-2 mm in width.

Any number of microstructures may be included in the microfluidic device for its intended purposes. In some embodiments, the microstructure layer may comprise about 2-10, 10-100, 100-1000 or more microstructures. In some embodiments, the microfluidic device may comprise about 2-8 inlet pools, preferably symmetrically distributed around the positioning well. In some embodiments, the device may further comprise an oil-holding layer connected to the cover layer and above the positioning well and inlet pools. In some embodiments, the device may further comprise a basal layer connected to the microstructure layer. In some embodiments, the basal layer, the microstructure layer, the cover layer and/or the oil-holding layer may be made of glass or polydimethylsiloxane (PDMS).

In another aspect, provided herein is a system for positioning a cell or organism, which comprises the microfluidic device disclosed herein and a cell or organism in the microstructure. Any suitable cell or organism may be included in the positioning system. In some embodiments, the cell may be selected from the group consisting of an animal cell, a plant cell, a fungal cell, a bacterial cell, a recombinant cell and a cultured cell. In some embodiments, the cell may be an oocyte, a neuron, or another cell type. In some embodiments, the organism may be a bacterium, yeast, C. elegans, etc. The positioning system may also include additional cells or organisms. In some embodiments, the system may further comprise a second type of cell or organism. Any detection device may also be included in the positioning system. In some embodiments, the system may further comprise an electrode in the microstructure.

C. Methods for Cell Motility Screening and/or Chemotaxis Testing

In a further aspect, provided herein is a method for in vitro fertilization, which comprises: a) adding a plurality of oocytes into the positioning well of the microfluidic device disclosed herein filled with a first fluid; b) letting said oocytes position in the microstructures; c) adding a plurality of sperms into the inlet pools; d) adding mineral oil into the oil-holding layer; and e) incubating said microfluidic device under suitable conditions for in vitro fertilization. In some embodiments, the method may further comprise: f) replacing the first fluid with a second fluid followed by further incubation. In some embodiments, the method may further comprise embryo in situ staining and/or retrieval.

Also provided herein is a method for determining how glial cells affect neurons, which comprises: a) adding a plurality of neurons into the positioning well of the microfluidic device disclosed herein filled with a first fluid; b) letting said neurons plant in the microstructures; c) adding a plurality of glial cells into the inlet pools; d) adding mineral oil into the oil-holding layer; and e) incubating said microfluidic device under suitable conditions for neuronal growth. In some embodiments, the method may further comprise: f) replacing the first fluid with a second fluid followed by further incubation. In some embodiments, different types of glial cells may be added into separate inlet pools, wherein the glial cells may be selected from the group consisting of astrocytes, microglia, oligodendrocytes and fibroblasts.

Further provided herein is a method for constructing a neural network, which comprises: a) adding a plurality of neurons into the positioning well of the microfluidic device disclosed herein filled with a first fluid; b) letting said neurons plant in the microstructures; c) adding mineral oil into the oil-holding layer; d) incubating said microfluidic device under suitable conditions for neuronal growth; and e) replacing the first fluid with a second fluid followed by further incubation. In some embodiments, each microstructure may comprise two columns, and the cross-section of each column may be arc-shaped and a wider-inside-narrower-outside gap exists between the two columns.

Any suitable incubation conditions may be used in the methods disclosed herein. In some embodiments, the suitable conditions may include humidification, about 25-37° C., and about 1-10% $CO_2$. A detection device may be used to detect cell growth in the methods disclosed herein. In some embodiments, the method may further comprise: i) placing a detection electrode inside the microstructure; ii) connecting the electrode to an external signal source and signal detection device; and iii) performing cell growth detection through analyzing electrical signals from the electrode. In some embodiments, the electrical signals may be voltage, current or impedance, etc.

Advantages of an exemplary microfluidic device disclosed herein include: 1) the microstructure can position a variety of cells/organisms, from cell lines to primary cells (such as oocyte, nerve cells and macrophages, etc.), to organisms (such as C. elegans, etc.); 2) since the position of each one or each group of cells/organisms is uniquely determined, the tracking of specified cell/organism can be achieved; 3) the microstructure can be in the form of multi-column structure and the gaps between columns can facilitate the cell/organism-environment communication, and cell-cell/organism-organism communication; 4) the design of the microstructure can be very flexible according to the size and characteristics of the cells/organism and has wide applications; 5) the electrical detection of cell/organism can be achieved when the positioning microstructure is integrated with electrodes with appropriate micro-machining process; 6) the device is suitable for cell motility screening and the screening is achieved through the inherent motility of samples in a stable environment, and centrifugation is avoided which might cause potential damages to samples; 7) the number, size and arrangement of the microchannels are quite flexible, in accordance with experimental requirement; 8) since the positioning well is accessible to the outer environment and it's easy to retrieve the positioned cells/organism; 9) the conditions of each specific cell/organism can be easily tracked and monitored when integrated with a variety of optical detection devices; 10) in situ detection of the positioned cells/organisms can be achieved in combination of fluorescence staining or other technologies; 11) the miniaturization of the device reduces the consumption of reagent and samples and is especially suitable for rare samples; 12) the device can be sterilized and sealed by mineral oil and thus can avoid or reduce pollution and reduce damages; 13) the layers of the microdevice can be made up of PDMS which can prevent or reduce the evaporation of water while is permeable for carbon dioxide and thus maintains a balanced system, moreover, each layer made of PDMS can be bonded together; and/or 14) the fabrication of the microfluidic device is simple and materials of the device are cost-saving and reusable, which is easy to promote for use in ordinary laboratories.

D. Examples

The following examples are offered to illustrate but not to limit the invention.

Example 1

Microfluidic Device

Figure 1:
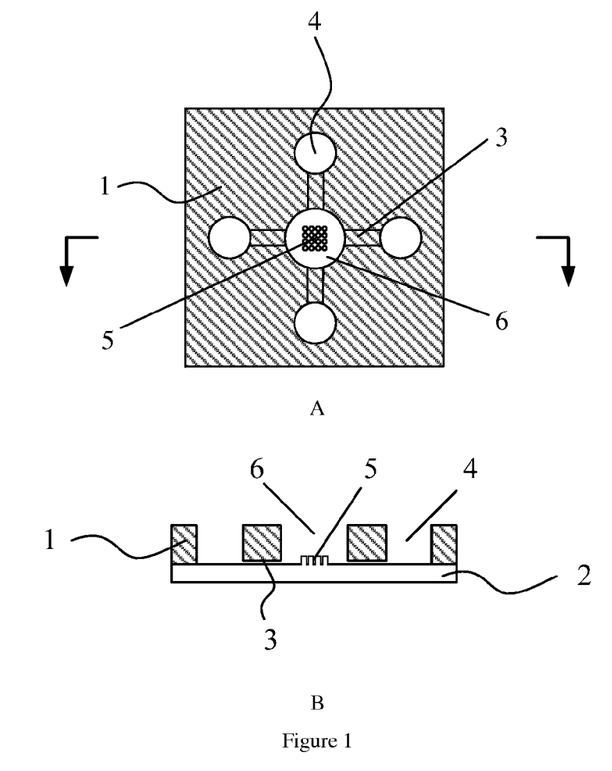
FIGS. 1A and 1B show schematic views of an exemplary microfluidic device. A) Top view of the exemplary microfluidic device; B) Sectional view of the exemplary microfluidic device.

In an exemplary embodiment shown in FIGS. 1A and 1B, the microfluidic device includes a microstructure layer 2 and a cover layer 1 and the cover layer 1 is connected closely to the microstructure layer 2. The microstructure layer 2 comprises one bottom layer and sixteen microstructures 5 on it. The microstructure 5 can position and hold samples (cell or organism). The cover layer 1 comprises one top layer, one positioning well 6 and four inlet pool 4. Four inlet pools are symmetrically distributed around the positioning well 6. The positioning well 6 is right above the microstructure 5 array and connected with each other. The inlet pool 4 and the positioning well 6 are connected by microchannel 3 which is formed between the microstructure layer 2 and the cover layer 1. Microchannel 3 can be formed either on the upper surface of microstructure layer 2 or on the lower surface of the cover layer 1 in some embodiments and formed both on the upper surface of microstructure layer 2 and on the lower surface of the cover layer 1 in other embodiments. In the exemplary embodiment described here, microchannel 3 is formed on the lower surface of the cover layer 1.

Figure 2:
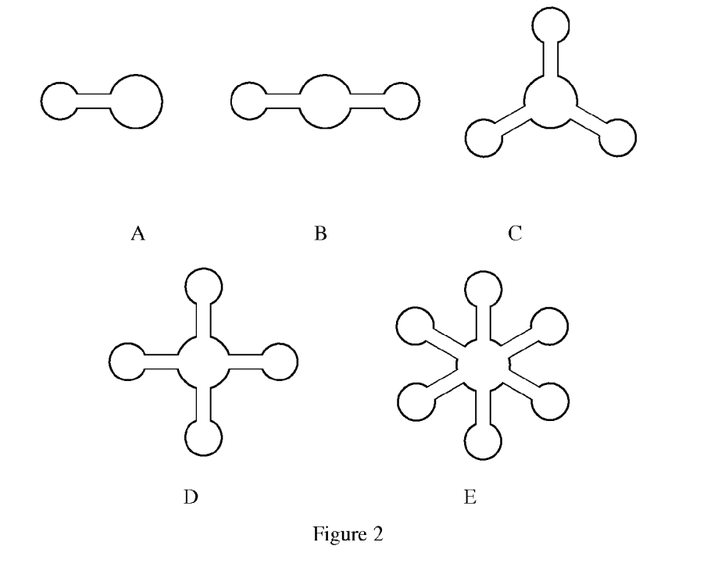
FIGS. 2A-2E show schematic views of an exemplary microfluidic device containing different number of microchannels and inlet pools. A) Exemplary microfluidic device containing one microchannel and one inlet pool; B) Exemplary microfluidic device containing two microchannels and two inlet pools; C) Exemplary microfluidic device containing three microchannels and three inlet pools; D) Exemplary microfluidic device containing four microchannels and four inlet pools; E) Exemplary microfluidic device containing six microchannels and six inlet pools.

In other embodiments, the number of the inlet pool 4 can be 1, 2, 3 or 6 etc. and the number of microchannel 3 will change accordingly (FIG. 2).

Figure 3:
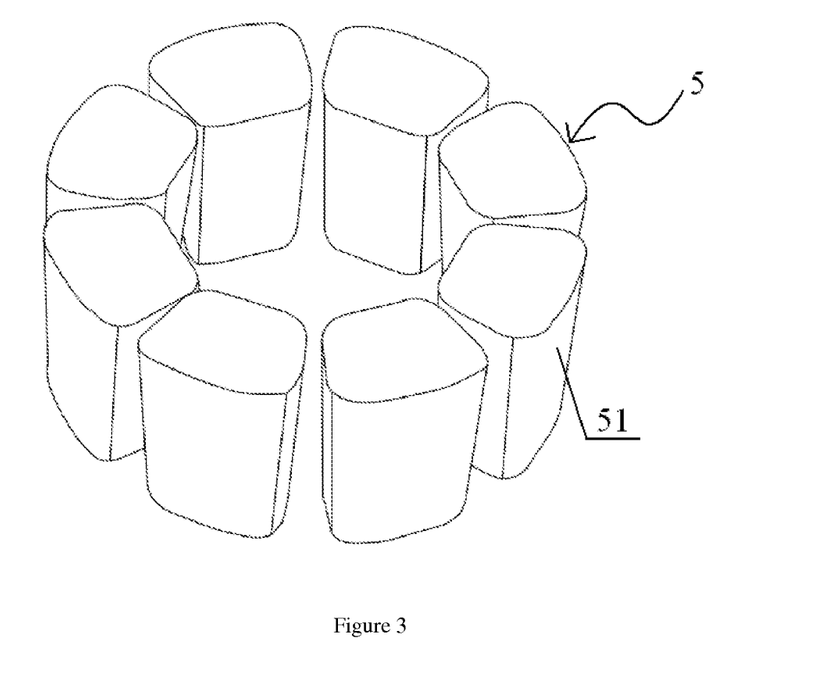
FIG. 3 is an illustration of an exemplary multi-column microstructure.

As shown in FIG. 3, the microstructure 5 is in the form of octa-columns structure and has eight columns 51. The cross-section of the microstructure 5 is partially closed circle as shown in FIG. 4B.

Figure 4:
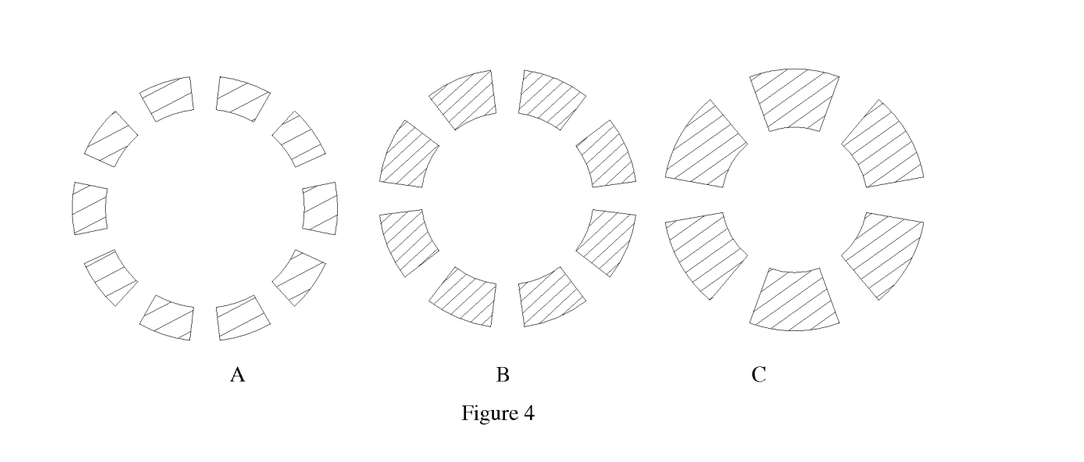
FIGS. 4A-4C show the sectional views of exemplary multi-column microstructures with partially closed circular cross-section. The cross section of each column is arc-shaped. A) Exemplary microstructure with ten columns; B) Exemplary microstructure with eight columns; C) Exemplary microstructure with six columns.
Figure 5:
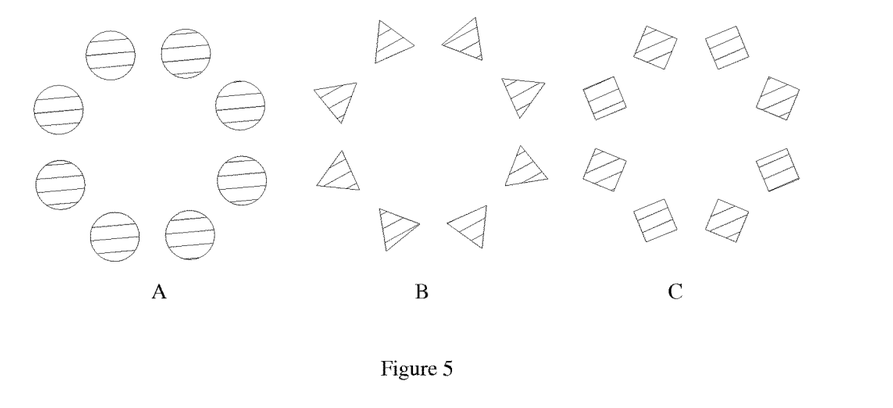
FIGS. 5A-5C show the sectional views of exemplary multi-column microstructures with partially closed circular cross-section. A) The cross section of each column is circular; B) The cross section of each column is triangular; C) The cross section of each column is square.
Figure 6:
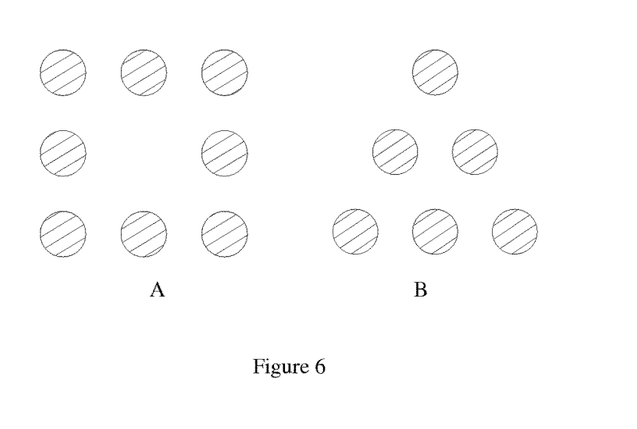
FIGS. 6A and 6B show the sectional views of exemplary multi-column microstructures with partially closed polygonal cross-section. A) The cross section of an exemplary microstructure is square; B) The cross section of an exemplary microstructure is triangular.
Figure 7:
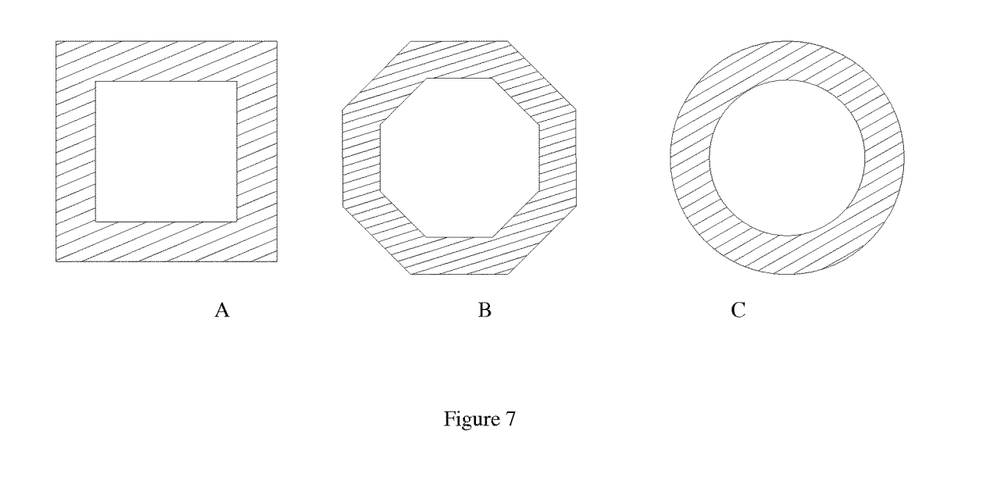
FIGS. 7A-7C show the sectional views of exemplary microstructures with closed circular or polygonal cross-section. A) The cross section of the exemplary microstructure is square; B) The cross section of the exemplary microstructure is octagonal; C) The cross section of the exemplary microstructure is circular.

In other embodiments, the cross-section of the column 51 can be circular, triangular and square; the number of columns 51 can be 10 or 6 as shown in FIGS. 4A and 4C; the cross-section of the microstructure 5 can be partially closed polygonal, such as square or triangular as shown in FIG. 6A and 6B; the cross-section of the microstructure 5 can be closed polygonal, such as square, octagonal or triangular as shown in FIGS. 7A-7C.

In this exemplary embodiment, the microstructure layer 2 and cover layer 1 are both made of PDMS which is quite permeable. PDMS can prevent or reduce the evaporation of water while is permeable for carbon dioxide and thus maintains a balanced system. Moreover, the microstructure layer 2 and cover layer 1 made of PDMS can be bonded together.

The microstructure 5 and microchannel 3 are constructed with standard photolithography and micromolding procedures. SU-8 photoresist is patterned onto a 4 inch silicon wafer to form a master, using printed film as a photomask. The SU-8 photoresist is concave for microstructure 5 and convex for microchannel 3. The thickness of SU-8 photoresist is set as 80 μm for microchannel 3 and 250 μm for microstructure 5. Liquid PDMS prepolymer solution is mixed by base and curing agent in a proportion of 10:1 and poured onto the master, cured at 72° C. for 1.5 h. The PDMS layers are then peeled off and bonded irreversibly together by oxygen plasma. The specific procedure of plasma bonding is: vacuum the chamber for 1 min, inject oxygen flow at 0.1 MPa for 1 min, turn on the plasma power after the oxygen flow stops for 5 s. After the glow is stable for 15 s, turn the power off and ventilate. Finally, the PDMS layers are taken out and pressed against each other to finish the bonding process.

The thickness of cover layer 1 determines the volume of inlet pool 4 and positioning well 6, as well as the concentration of samples and volume of the culturing system. In this exemplary embodiment, cover layer 1 is 5 mm thick while microstructure layer 2 is 3 mm thick; the diameter of the inlet pool 4 is 4 mm while the diameter of the positioning well 6 is 6 mm; microchannel 3 is 80 μm in depth, 9 mm in length and 1.5 mm in width. The depth of the microstructure 5 is 250 μm and the gaps between columns 51 should be able to prevent the oocyte or organism to flow outside of the microstructure which is set as 50 μm in this exemplary embodiment.

Example 2

Microfluidic Chips

Figure 8:
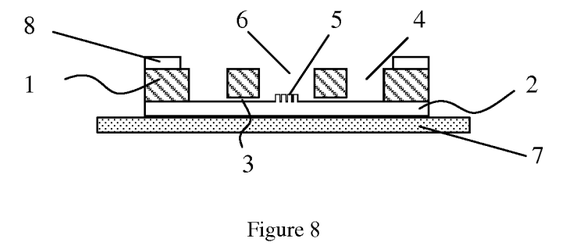
FIG. 8 shows a sectional view of an exemplary microfluidic device.

As shown in FIG. 8, the difference between this exemplary embodiment and Example 1 lies in: there is one basal layer 7 connected to the microstructure layer 2; there is one oil-holding layer 8 connected to the cover layer 1, right above the positioning well 6 and inlet pool 4. Basal layer 7 is made of glass and oil-holding layer 8 is made of PDMS. Oil-holding layer 8 is a PDMS slice whose size exactly matches with cover layer 1 with a hole to hold mineral oil.

Example 3

In Vitro Fertilization

This exemplary example utilized the microdevice in Example 2 to realize the integration of single oocyte positioning, mouse sperm motility screening, in vitro fertilization, medium replacement, early mouse embryo culturing, embryo in situ staining and embryo retrieval. Using the microfluidic device included the following steps:

1) Before use the entire device was cleaned with ultrasonic washer and sterilized by UV (30 min). Then the device was oxygen plasma treated to improve the hydrophilicity. The specific procedure of oxygen plasma treatment was: vacuum the chamber for 1 min, inject oxygen flow at 0.1 MPa for 1 min, and turn on the plasma power after the oxygen flow stops for 5 s. After the glow was stable for 15 s, turn the power off and ventilate. The entire microfluidic device was prefilled with HTF (Human tubal fluid).

Figure 9:
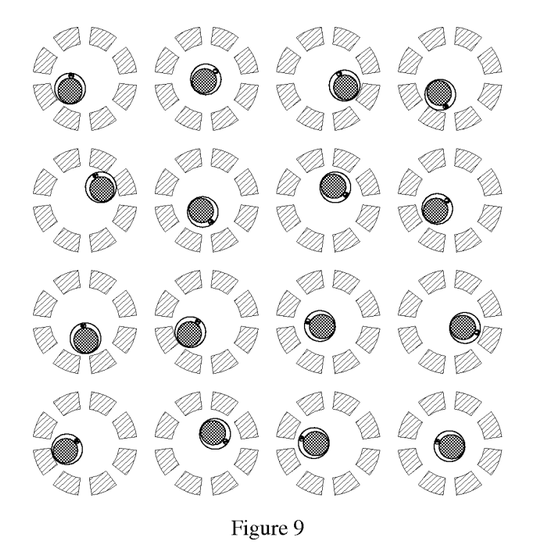
FIG. 9 is an illustrative view of single oocyte positioning in exemplary microstructures.

2) Mouse single oocyte positioning: every denuded oocyte was directly pipetted into microstructure 5 inside positioning well 6. Once the oocyte was dropped into the structure, the gravity would guide the oocyte to sink down to the bottom. FIG. 9 illustrates the array loaded with 16 (4×4) singly positioned oocytes.

3) Mouse sperm motility screening: Approximately 2.5× $10^4$ sperm (ICR mouse, capacitated for 30 min under 37° C.) were added into each of the inlet pool 4. The motile sperm could swim through the microchannel 3 spontaneously to reach for the central positioning well 6. It was important to avoid turbulence of the fluid, so it was necessary to take out 2.5 μl medium from inlet pool 4 immediately after adding 2.5 μl sperms.

Figure 10:
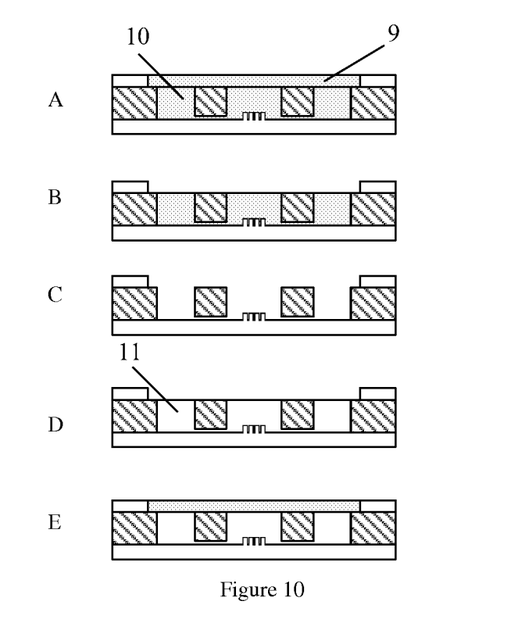
FIGS. 10A-10E are a flow chart illustrating an exemplary medium replacement process.

4) In vitro fertilization: Mineral oil 9 was laid into oil-holding layer 8 to seal the entire microchannel system (as shown in FIG. 10A). During fertilization, the whole device was cultured in conventional $CO_2$ incubator (humidified, 37° C., 5% $CO_2$) to maintain a stable environment.

5) Medium replacement: After fertilization, mineral oil 9 was taken out from the surface and HTF medium was withdrawn from all inlet pools by pipetting. Embryo culturing medium (KSOM medium) 11 was then added in the inlets and the pressure caused by the difference of liquid levels would drive the liquid system to reach new equilibrium. Mineral oil 9 was laid again into oil-holding layer 8 and the whole process is shown in FIGS. 10A-10E. After medium replacement, the unattached or dead sperm was removed out, which could produce a fresh and favorable environment for the embryonic development.

6) Embryo development tracking: Since every layer was made of PDMS or glass which were both transparent, each single embryo could be easily photographed under an optical microscope for its growth status.

Figure 11:
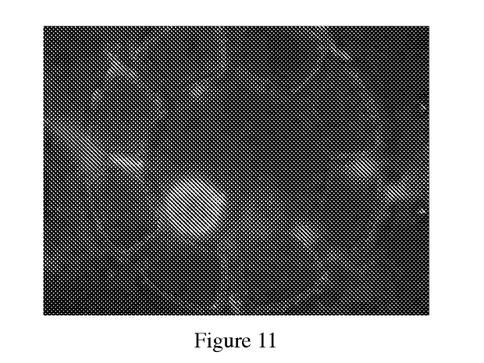
FIG. 11 is a fluorescent staining picture of an embryo in an exemplary microstructure.

7) Embryo in situ staining: In situ detection of the positioned embryos was achieved by adding fluorescence dye into inlet pool 4. FIG. 11 is an in situ fluorescent staining picture of embryos.

8) Embryo retrieval: Since the positioning well was accessible to the outer environment and it's easy to retrieve the positioned embryos from microstructures through pipetting.

Example 4

Application in Determining how Glial Cells Affect Neurons

Figure 12:
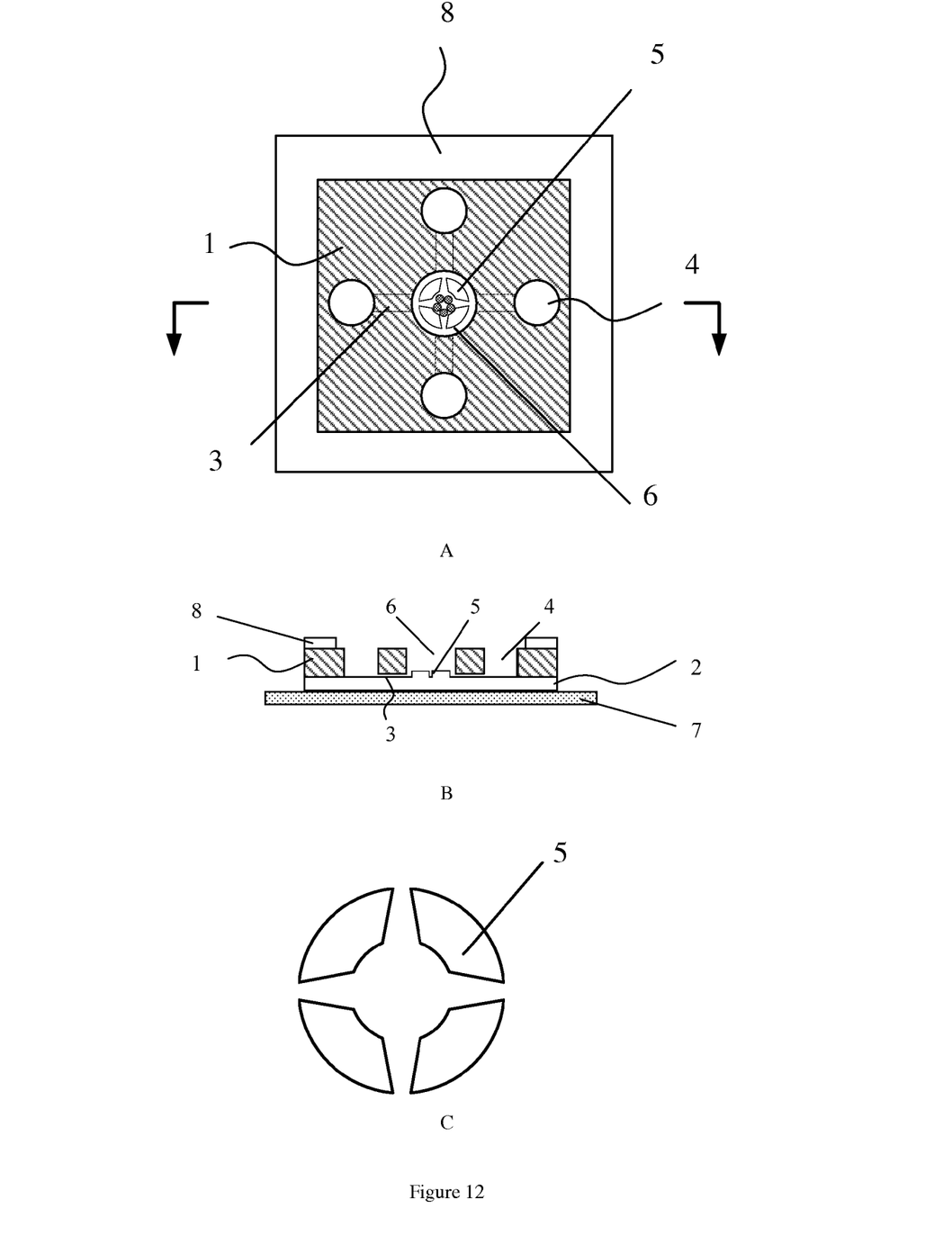

The microfluidic device in this exemplary embodiment, similar to the one in Example 2, comprises four layers: basal layer, microstructure layer, cover layer and oil-holding layer (as shown in FIG. 12A). The difference exists that there is only one microstructure in this device and this microstructure comprises four columns. The cross-section of each column is arc-shaped and a wider-inside-narrower-outside gap exists between each two adjacent columns to guide the growth of neural synapses (FIGS. 12B and 12C). The microstructure is 250 μm high, and has an inner diameter of 4 mm and outer diameter 4.2 mm. The gap structure has an inner arc length of 50 μm and outer arc length of 30 μm.

Studying how different glial cells affect neurons with the microfluidic device included the following steps:

1) Device pretreatment: the same as in Example 3, the entire device is cleaned with ultrasonic washer and sterilized by UV. Then the device is oxygen plasma treated to improve the hydrophilicity. The entire microfluidic device is coated overnight with 50 μg/ml poly-L-lysine solution and then prefilled with neuron-glia culture medium. Here we use MEM and Newobasal medium, with 5% fetal bovine serum, 1% B27, 0.5% sodium pyruvate, 0.25% L-glutamine, 0.5% Penicillin/Streptomycin and 0.5% glucose.

2) Cell collection: In accordance with standard procedures, neurons are separated and prepared from cerebral cortex of fetal rat at embryonic day 17-18 (*J. Neurochem.* (1978) 31:887-94); in accordance with standard procedures (McCarthy and Vellis, *J. Cell Biol.* (1980) 85:890-902), astrocytes, microglia, oligodendrocytes and fibroblasts are separated and prepared from newborn rat cerebral cortex. Single suspensions of astrocytes, microglia, oligodendrocytes and fibroblasts are obtained through successive purifications and validated with cell-type-specific antibodies.

Figure 13:
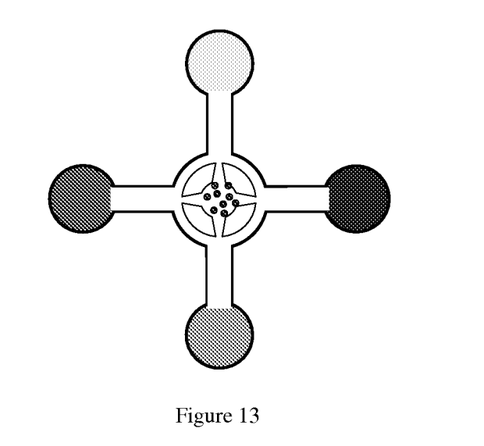
FIG. 13 illustrates the experimental design in Example 4.

3) Cell plantation: neuron suspension is added into microstructure by pipetting carefully without disturbance of the liquid, at a density of approximately $0.5-1\times10^6$/ml. Cells adhere 24 hours after plantation. Then, add astrocytes, microglia, oligodendrocytes and fibroblasts into four inlet pools at a density of approximately $0.5-1\times10^6$/ml by pipetting (as shown in FIG. 13).

4) Cell culture: Seal the entire system by mineral oil or other kind of oil and put the device in conventional $CO_2$ incubator (humidified, 37° C., 5% $CO_2$).

5) Medium replacement: Change medium every 2 to 3 days. Firstly, take mineral oil out from the surface and withdraw the old medium from all inlet pools by pipetting. Secondly, add fresh medium in the inlet pools and the pressure caused by the difference of liquid levels will drive the liquid system to reach new equilibrium. The medium will be mostly replaced after three runs of medium changing.

6) Detection: Examine the growth pattern of neurons by optical microscope. Neurons will exhibit a preference of growing towards a special direction if the glial cells in that direction have a beneficial effect for neurons.

Example 5

Application in Constructing Neural Network

Figure 14:
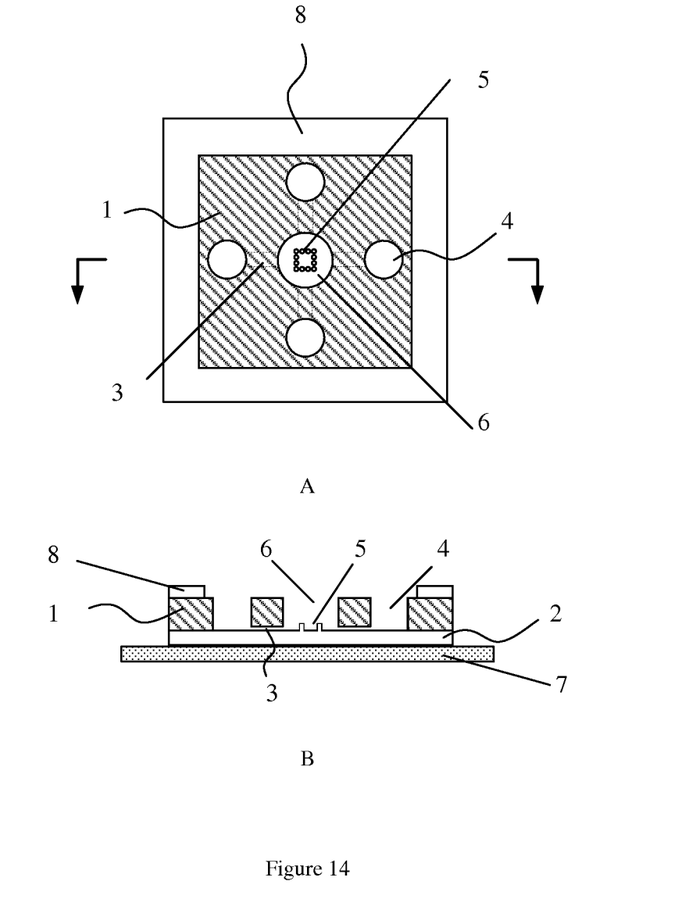
FIGS. 14A and 14B show schematic views of an exemplary microfluidic device. A) Top view of the exemplary microfluidic device; B) Sectional view of the exemplary microfluidic device.
Figure 15:
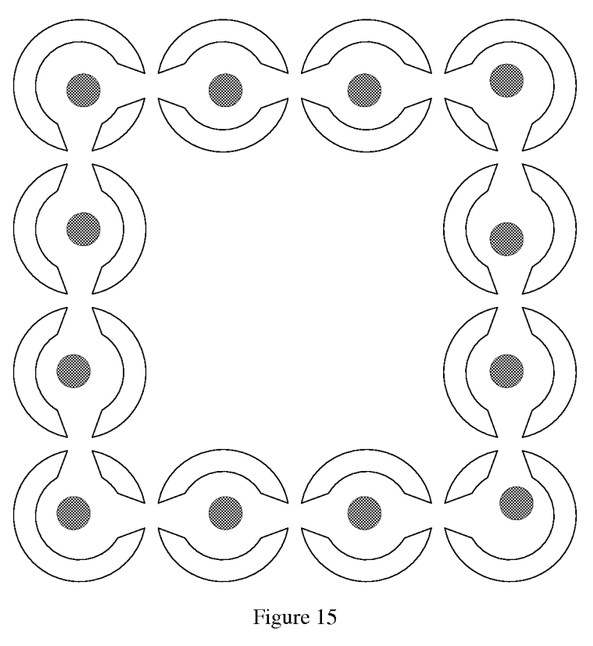
FIG. 15 illustrates an exemplary microstructure design.

The microfluidic device in this exemplary embodiment, similar to the one in Example 2, comprises four layers: basal layer, microstructure layer, cover layer and oil-holding layer (as shown in FIG. 14). The difference exists that there is 12 microstructures in this device and each microstructure comprises two columns. The cross-section of each column is arc-shaped and a wider-inside-narrower-outside gap exists between the two columns (FIG. 15). The microstructure is 250 μm high, and has an inner diameter of 100 μm and outer diameter 160 μm. The gap structure has an inner arc length of 5 μm and outer arc length 3 μm.

Application of the microfluidic device in constructing specific neural network includes the following steps:

1) Device pretreatment: the same as in Example 3, the entire device is cleaned with ultrasonic washer and sterilized by UV. Then the device is oxygen plasma treated to improve the hydrophilicity. The entire microfluidic device is coated overnight with 50 μg/ml poly-L-lysine solution and then prefilled with neuron-glia culture medium. Here we use MEM and Newobasal medium, with 5% fetal bovine serum, 1% B27, 0.5% sodium pyruvate, 0.25% L-glutamine, 0.5% Penicillin/Streptomycin and 0.5% glucose.

2) Cell collection: In accordance with standard procedures, neurons are separated and prepared from cerebral cortex of fetal rat at embryonic day 17-18. The purity of the cell suspension is validated with neuron-specific antibodies.

3) Cell plantation: About 10 to 20 neurons are added into microstructures by pipetting carefully without disturbance of the liquid (as shown in FIG. 15).

4) Cell culture: Seal the entire system by mineral oil or other kind of oil and put the device in conventional $CO_2$ incubator (humidified, 37° C., 5% $CO_2$).

5) Medium replacement: Neurons will adhere after 24 hours of incubation and the medium should be changed every 1 to 2 days. Firstly, take mineral oil out from the surface and withdraw the old medium from all inlet pools by pipetting. Secondly, add fresh medium in the inlet pools and the pressure caused by the difference of liquid levels will drive the liquid system to reach new equilibrium. The medium will be mostly replaced after three runs of medium changing.

6) Detection: Examine the growth pattern of neurons by optical microscope. As shown in FIG. 15, the two gaps of each microstructure will guide neurons to grow synapses in that way and form contact one by one. In this way, a closed circle is formed by neurons in 12 microstructures and an artificially simulated neural network is constructed.

Example 6

Application in Electrical Detection

Figure 16:
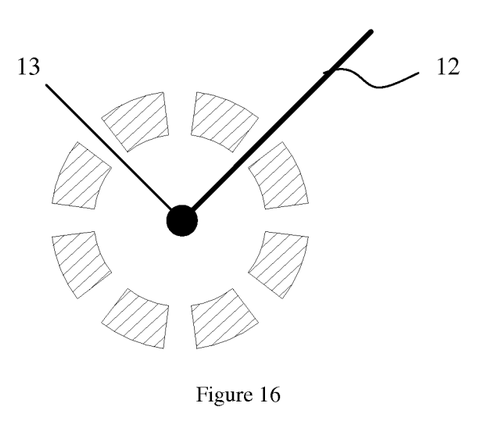
FIG. 16 illustrates the integration of an exemplary microstructure with the detection electrode.

As shown in FIG. 16, detection electrode 13 is placed in the center of microstructure 5 and directed out by wire 12 to external signal source and signal detection devices. The growth conditions of cells in microstructure 5 can be real-time detected through analyzing the electrical signals (voltage, current, impedance, etc.).

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A system for positioning a cell or organism, which comprises:
   a microfluidic device comprising:
   a) a microstructure layer comprising a bottom layer and a plurality of microstructures on said bottom layer, wherein each of the microstructures comprises a plurality of columns on said bottom layer; and
   b) a cover layer comprising a positioning well and at least one inlet pool, wherein said at least one inlet pool and said positioning well are in fluid connection by a microchannel between said microstructure layer and said cover layer,
   wherein said cover layer is connected to said microstructure layer to form said microchannel, said microchannel being provided on the upper surface of said microstructure layer and/or on the lower surface of said cover layer, and said positioning well aligns with and is in fluid connection with said microstructures; and
   a cell or organism in at least one of the plurality of microstructures.

2. The system of claim 1, wherein the cell is selected from the group consisting of an animal cell, a plant cell, a fungal cell, a bacterial cell, a recombinant cell and a cultured cell.

3. The system of claim 2, wherein the cell is an oocyte or a neuron.

4. The system of claim 1, wherein the organism is a bacterium, yeast, or *C. elegans*.

5. The system of claim 1, wherein the cell or organism is a first type of cell or organism, and wherein a second type of cell or organism is provided in said at least one inlet pool.

6. The system of claim 1, further comprising an electrode in at least one of the microstructures.

7. The system of claim 1, wherein the cross-section of at least one of the microstructures is closed or partially closed.

8. The system of claim 1, comprising at least two inlet pools symmetrically distributed around the positioning well.

9. The system of claim 1, wherein the depth of at least one of the microstructures is larger than the diameter of the cell or organism.

10. The system of claim 9, wherein the depth of at least one of the microstructures is about 10-500 μm.

11. The system of claim 1, further comprising an oil-holding layer connected to the cover layer and above the positioning well and the at least one inlet pool.

12. The system of claim 1, further comprising a basal layer connected to the microstructure layer.

13. The system of claim 1, wherein the cross-section of each column is arc-shaped, square, triangular, or circular.

14. The system of claim 1, wherein a gap exists between adjacent columns of each of the microstructures, and the gap is smaller than the diameter of the cell or organism.

15. The system of claim 1, wherein each of the microstructures comprises 2, 4, 6, 8, 10 or more columns on the bottom layer.

16. The system of claim 15, wherein each microstructure comprises two columns, the cross-section of each column is arc-shaped, and a wider-inside- narrower-outside gap exists between the two columns.

17. A method for in vitro fertilization, which comprises:
   a) providing the system of claim 1, which further comprises an oil-holding layer connected to the cover layer and above the positioning well and the at least one inlet pool, wherein the system is filled with a first fluid, and wherein the cell is an oocyte positioned in at least one of the microstructures;
   b) adding a plurality of sperms into the at least one inlet pool;
   c) adding a mineral oil into the oil-holding layer; and
   d) incubating said system for in vitro fertilization.

18. The method of claim 17, wherein the system is incubated under humidification, about 25-37° C., and about 1-10% $CO_2$.

19. The method claim 17, further comprising:
   e) replacing the first fluid with a second fluid followed by further incubation.

20. The method claim 17, further comprising embryo in situ staining and/or retrieval.

21. A method for determining how glial cells affect neurons, which comprises:
   a) providing the system of claim 1, which further comprises an oil-holding layer connected to the cover layer and above the positioning well and the at least one inlet pool, wherein the system is filled with a first fluid, and wherein the cell is a neuron positioned in at least one of the microstructures;
   b) letting said neuron in step a) plant in the microstructures;
   c) adding a plurality of glial cells into the at least one inlet pool;
   d) adding a mineral oil into the oil-holding layer; and
   e) incubating said system for neuronal growth.

22. The method of claim 21, wherein the system is incubated under humidification, about 25-37° C., and about 1-10% $CO_2$.

23. The method of claim 21, further comprising:
   f) replacing the first fluid with a second fluid followed by further incubation.

24. The method of claim 21, wherein the microfluidic device comprises at least two inlet pools and different types of glial cells are added into separate inlet pools.

25. The method of claim 24, wherein the glial cells are selected from the group consisting of astrocytes, microglia, oligodendrocytes and fibroblasts.

26. A method for constructing a neural network, which comprises:
   a) providing the system of claim 1, which further comprises an oil-holding layer connected to the cover layer and above the positioning well and the at least one inlet pool, wherein the system is filled with a first fluid, and wherein the cell is a neuron positioned in at least one of the microstructures;
   b) letting said neuron in step a) plant in the microstructures;

c) adding a mineral oil into the oil-holding layer;
d) incubating said system for neuronal growth; and
e) replacing the first fluid with a second fluid followed by further incubation.

27. The method of claim 26, wherein the system is incubated under humidification, about 25-37° C., and about 1-10% $CO_2$.

28. The method of claim 26, wherein each microstructure comprises two columns, and the cross-section of each column is arc-shaped and a wider-inside- narrower-outside gap exists between the two columns.

29. The method of claim 26, further comprising:
  i) placing a detection electrode inside at least one of the microstructures;
  ii) connecting the electrode to an external signal source and signal detection device; and
  iii) performing cell growth detection through analyzing electrical signals from the electrode.

30. The method of claim 29, wherein the electrical signals are voltage, current, or impedance.

* * * * *